(12) United States Patent
Perera et al.

(10) Patent No.: US 12,239,575 B2
(45) Date of Patent: Mar. 4, 2025

(54) METHOD AND APPARATUS FOR SHEARING TISSUE AT A TARGET SURGICAL SITE

(71) Applicants: SINGAPORE HEALTH SERVICES PTE LTD, Singapore (SG); Michael Belkin, Givat Shmuel (IL)

(72) Inventors: Shamira Perera, Singapore (SG); Michael Belkin, Givat Shmuel (IL); Alvin Kok, Singapore (SG)

(73) Assignee: SINGAPORE HEALTH SERVICES PTE LTD, Singapore (SG)

( * ) Notice: Subject to any disclaimer, the term of this patent is extended or adjusted under 35 U.S.C. 154(b) by 938 days.

(21) Appl. No.: 16/970,942

(22) PCT Filed: Feb. 15, 2019

(86) PCT No.: PCT/SG2019/050089
§ 371 (c)(1),
(2) Date: Aug. 18, 2020

(87) PCT Pub. No.: WO2019/160508
PCT Pub. Date: Aug. 22, 2019

(65) Prior Publication Data
US 2020/0390600 A1    Dec. 17, 2020

Related U.S. Application Data

(60) Provisional application No. 62/631,960, filed on Feb. 19, 2018.

(51) Int. Cl.
*A61F 9/007* (2006.01)
*A61B 10/02* (2006.01)
*A61F 9/008* (2006.01)

(52) U.S. Cl.
CPC ...... *A61F 9/00763* (2013.01); *A61B 10/0266* (2013.01); *A61B 10/0283* (2013.01);
(Continued)

(58) Field of Classification Search
CPC .. A61F 9/007; A61F 9/00709; A61F 9/00736; A61F 9/00745; A61F 9/00754;
(Continued)

(56) References Cited

U.S. PATENT DOCUMENTS 3,844,272 A    10/1974  Banko
4,573,979 A     3/1986  Blake
(Continued)

FOREIGN PATENT DOCUMENTS

CN    101677823 A    3/2010
EP      2100562 A2   9/2009
(Continued)

*Primary Examiner* — Katherine M Shi
(74) *Attorney, Agent, or Firm* — SOROKER AGMON NORDMAN PTE LTD

(57) ABSTRACT

A surgical tool for shearing tissue at a target surgical site, the surgical tool comprising a cannula assembly with a distal end and a proximal end, a cannula opening into the lumen of the cannula at the distal end, a cutting device coupled to the distal end and within the cannula opening, and an axial ball joint coupled to the proximal end of the cannula assembly, that when rotated, causes the cutting device at the distal end to rotate about a longitudinal axis passing axially through the lumen of the cannula assembly, so as to shear a portion of tissue at a target surgical site.

17 Claims, 9 Drawing Sheets

(52) U.S. Cl.
CPC .... *A61F 9/00821* (2013.01); *A61B 2217/007* (2013.01); *A61F 2009/00868* (2013.01); *A61F 2009/00891* (2013.01)

(58) Field of Classification Search
CPC ............. A61F 9/00763; A61B 10/0266; A61B 10/0283; A61B 17/320016; A61B 17/32002; A61B 17/320036; A61B 2017/32004; A61B 17/320758; A61B 2217/005; A61B 2217/007; A61B 17/320783; A61B 2017/320084
See application file for complete search history.

(56) References Cited

U.S. PATENT DOCUMENTS

| | | | |
|---|---|---|---|
| 4,672,965 A | 6/1987 | Baum | |
| 4,708,147 A * | 11/1987 | Haaga | A61B 10/0266 600/566 |
| 2002/0151835 A1 | 10/2002 | Ross et al. | |
| 2006/0030785 A1 * | 2/2006 | Field | A61B 10/0275 600/567 |
| 2017/0333252 A1 | 11/2017 | Biancalana et al. | |
| 2018/0296237 A1 * | 10/2018 | Slupchynskyj | A61B 17/32093 |
| 2020/0281766 A1 | 9/2020 | Berlin | |

FOREIGN PATENT DOCUMENTS

| | | | | |
|---|---|---|---|---|
| EP | 2754427 A1 | 7/2014 | | |
| GB | 1349881 A | 4/1974 | | |
| JP | 2017029240 A | 2/2017 | | |
| WO | 02056805 A2 | 7/2002 | | |
| WO | WO-2008080149 A1 * | 7/2008 | ......... | A61F 9/00754 |
| WO | 2012162493 A2 | 11/2012 | | |

* cited by examiner

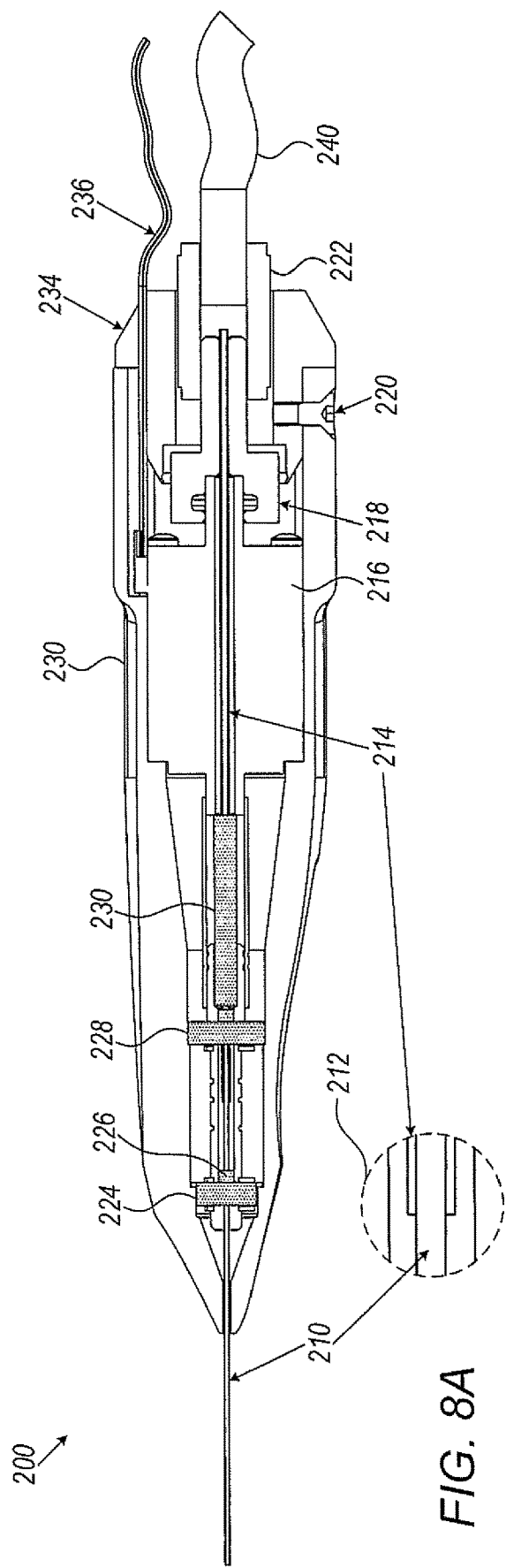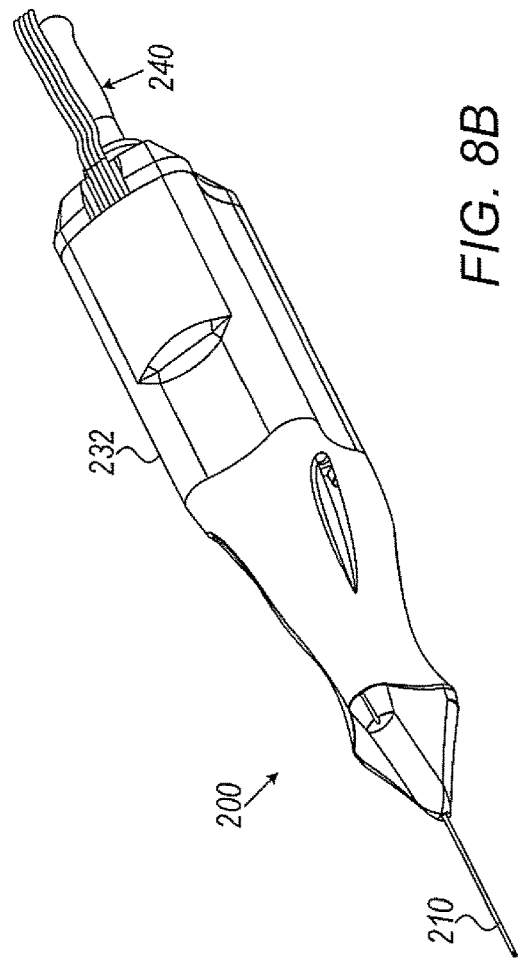
FIG. 8A
FIG. 8B

METHOD AND APPARATUS FOR SHEARING TISSUE AT A TARGET SURGICAL SITE

FIELD OF THE INVENTION

The present invention relates to surgical tools, and more specifically to method and apparatus for shearing tissue at a target surgical site.

BACKGROUND OF THE INVENTION

Glaucoma is a group of diseases characterized by progressive atrophy of the optic nerve head leading to visual field loss, and ultimately, blindness. Glaucoma is often associated with elevated intraocular pressure (IOP), which is the most important risk factor for visual field loss progression because it damages the optic nerve fibers via multiple mechanisms. Other causes of glaucoma may be that the nerve is particularly vulnerable to the intraocular pressure due to poor local circulation, tissue weakness or abnormality of structure. In a "normal" eye, intraocular pressure ranges from 10 to 21 mm mercury. In an eye with glaucoma, the pressure can rise to as much as 75 mm mercury. The TOP is the only treatable aspect of glaucoma and its successful reduction is effective in slowing the progression of the disease.

There are several types of glaucoma, including primary open angle (POAG) and angle closure glaucoma, which involve the abnormal increase in intraocular pressure, primarily by obstruction of the outflow of aqueous humor from the eye. The most prevalent type is primary open angle glaucoma in which the aqueous humor has free access to the iridocorneal angle, but aqueous humor drainage is impaired due to obstruction of the trabecular meshwork (TM). Angle closure glaucoma is particularly common in Asians, and may be treated initially by surgical removal of the lens or by a laser peripheral iridotomy. Once this is done, to open up the angle, the remaining angle is potentially amenable to angle surgery as for OAG, but the results may be more modest due to downstream damage to the collector channels and beyond. Less prevalent types of glaucoma include secondary glaucomas related to inflammation, trauma, and hemorrhage. These may also be more difficult to treat due to downstream damage or because multiple mechanisms are at play.

OAG is caused by a blockage in the trabecular meshwork. This leads to an increase in intraocular pressure. The major obstruction is at the juxta-canalicular portion, which is situated adjacent to Schlemm's canal (SC). An operation (trabeculotomy) can be performed in which a small needle or probe is introduced into Schlemm's canal and the trabecular meshwork is mechanically disrupted opening the canal to the anterior chamber (AC). Approximately 90°-120° of trabecular meshwork can be thus disrupted in order to facilitate egress of the aqueous humor into the canal thereby reducing the intraocular pressure.

All current treatments for OAG consist of reducing intraocular pressure (IOP). Initial treatment involves administration of eye drops to facilitate the outflow or increase outflow of aqueous humor, such as prostaglandin analogues, beta-blockers, carbonic anhydrase inhibitors and others. Pharmacological treatment is prohibitively expensive for a large majority of glaucoma patients especially in the longer term and. In addition, many people afflicted with the disease live in remote or undeveloped areas where the drugs are not readily accessible. The drugs used in the treatment often have undesirable side effects. Furthermore, over 50 percent of patients do not use their medications at all or do it suboptimally meaning that adherence and persistence to complex regimes of drops is difficult.

When medications fail (e.g., eye drop therapies stop working), gauged by the ineffectiveness in reducing TOP or low compliance, laser or surgical therapies may then be used. Laser surgery for glaucoma, while non-invasive, is restricted to well-equipped large eye hospitals. The procedure has three major drawbacks. First, it may not always lower pressure in the eye with a 20% failure rate. Secondly, its effect is not permanent with the IOP reduction observed lasting from months to five years in the best case scenario. Thirdly, laser surgery may create scarring at the back of the trabecular mesh. Furthermore, patients are forced to turn to conventional surgery options when laser surgery is no longer an option.

The most common operation to reduce IOP is guarded filtration surgery (trabeculectomy), where a fistula created through the limbal sclera is protected by an overlying partial thickness sutured scleral flap. The sclera flap provides additional resistance to excessive loss of aqueous humor from the eyeball, thereby reducing the risk of early postoperative hypotony. However, scarring is very prevalent, particularly in the Asian population and requires the common use of anti-fibrotic agents to limits its deleterious effects whilst balancing this against the toxicity of these agents to the remainder of the ocular tissues.

Various attempts have been and are being made to overcome the problems of filtration surgery, for example, by using ophthalmic implant instruments such as various minimally invasive procedures and implants, which are mostly in development and are only partially effective. Later on glaucoma drainage devices such as the Mimed glaucoma drainage devices are used. Such devices typically include drainage tubes, so as to maintain the integrity of the openings formed in the eyeball for the relief of the IOP. Such drainage devices suffer from several disadvantages. For example, the implants may utilize a valve mechanism for regulating the flow of aqueous humor from the eyeball; defects in and/or failure of such valve mechanisms could lead to excessive egress of aqueous and possible hypotony. These devices tend to fail over time, from subconjunctival scarring.

Additionally, the typical implant insertion operation is complicated, costly and takes a long time. It is usually reserved for complex glaucoma problems, those with pre-existing scarring or redo operations. More recently there has been an expansion in the use of minimally invasive glaucoma surgery (MIGS), which involves various implants being inserted into the iridocorneal angle to bypass the trabecular meshwork blockage. These are expensive and require some additional skills. These devices typically address the blockage in the trabecular meshwork, but have the problem of limited efficacy although they are much safer than trabeculectomy. They are commonly used in conjunction with cataract surgery. Of the MIGS that target the trabecular meshwork, some are blades which ship the TM away over 120 degrees but there are concerns over how much damage is done to the back wall of the canal and in the collateral damage to other tissues.

Others are implants which sit in the canal and not only bypass the TM but also expand the canal. Some implants in the trabecular meshwork have been shown to have more dramatic IOP lowering effects when more are placed in the TM, but of course this adds to the cost. Some of the more difficult-to-use type of MIGS involve using a fiber optic catheter which are inserted into the canal and passed 360 degrees. Viscoelastic is used to expand the canal and the collector channels as the catheter is withdrawn leaving no implant in the eye. Finally, the U.S. Food and Drug Administration (FDA) has currently withdrawn one suprachoroidal implant from the market due to deleterious effects on the endothelial cells of the cornea.

When all these fail, other forms of treatment have included physical or thermal destruction ("cyclodestruction") of the ciliary body of the eye, commonly by application of a laser, or high frequency ultrasound to reduce the secretion of the aqueous humor to the eye thereby reducing the IOP. This is reserved for poorly seeing eyes as it can lead to further vision loss and the effects can be unpredictable, with redo procedures and overtreatment leading to hypotony still being observed too often.

A relatively new technology, Excimer Laser Trabeculotomy (ELT) ab interno using a XeCl Excimer Laser with an emission wavelength of 308 nm. ELT was developed to enhance the outflow facility by creating 0.5-mm holes through the anterior meshwork in the inner wall of Schlemm's canal. This technology involves the use of a very expensive large laser with very toxic gasses. Since the 308 nm wavelength is not transmitted by water. The laser beam is applied to the TM through a probe inserted into the anterior chamber to touch the TM creating a 0.5 mm or larger hole. This is repeated 6-10 times without removing the probe from the eye. ELT is very effective in reducing IOP but is not commonly available due to the price and complexity of the instrument.

In view of the limited effectiveness of treatment options, there is, thus, a need for more effective, repeatable, no implant, and less destructive glaucoma treatments, particularly treatments that do not destroy or touch the back wall of the trabecular meshwork of the eye.

SUMMARY OF THE INVENTION

There is thus provided, in accordance with some embodiments of the present invention, a surgical tool for shearing tissue at a target surgical site. The surgical tool may include a cannula assembly with a distal end and a proximal end, a cannula opening into a lumen of the cannula assembly at the distal end, a cutting device coupled to the elongated tube at the distal end and within the cannula opening, and an axial ball joint. The axial ball joint in the body of the surgical tool, may be coupled to the proximal end of the cannula assembly, that when rotated, causes the cutting device at the distal end to rotate about the longitudinal axis passing axially through the lumen of the cannula assembly, so as to shear a portion of tissue at a target surgical site.

Furthermore, in accordance with some embodiments of the present invention, the target surgical site is a trabecular meshwork of an eye of a subject.

Furthermore, in accordance with some embodiments of the present invention, the distal end of the cannula assembly has a curved inward profile.

Furthermore, in accordance with some embodiments of the present invention, the distal end of the cannula assembly has a beveled tip.

Furthermore, in accordance with some embodiments of the present invention, the surgical tool may include au outer tube where the cannula assembly is placed within die outer tube passing axially along the longitudinal axis and the cannula assembly is rotatable within the outer tube.

Furthermore, in accordance with some embodiments of the present invention, the outer tube is not rotatable.

Furthermore, in accordance with some embodiments of the present invention, the cutting device extends radially mid-way within the cannula or is flush with the cannula opening.

Furthermore, in accordance with some embodiments of the present invention, the cutting device is a surgical cutting blade.

Furthermore, in accordance with some embodiments of the present invention, the cutting device is a cutting wire.

There is further provided, in accordance with some embodiments of the present invention, a surgical tool for shearing tissue at a target surgical site. The surgical tool may include a cannula assembly, a surgical blade, a connector hub, and an axial ball joint. The cannula assembly with a distal end and a proximal end, may include au elongated tube within a flexible sheath along a longitudinal axis passing axially through a first lumen of the elongated tube. A second lumen may be formed between the sheath and the elongated tube along the longitudinal axis. The surgical blade may be coupled to the elongated tube at the distal end. The connector hub attached to a body of the surgical tool may include a central inner hub hole and one or more outer hub holes coupled to the cannula assembly at the proximal end. The elongated tube may be placed within the central inner hub hole in the connector hub. The one or more outer hub holes in the connector hub may be coupled to the second lumen. The axial ball joint in the body of the surgical tool, may be coupled to the elongated tube at the proximal end of the cannula assembly, that when rotated, causes the surgical blade at the distal end to rotate about the longitudinal axis, so as to shear a portion of tissue at a target surgical site.

Furthermore, in accordance with some embodiments of the present invention, the sheared portion may include eye tissue excised from a trabecular meshwork of an eye.

Furthermore, in accordance with some embodiments of the present invention, the surgical tool may include a biopsy collection chamber in the body for collecting the sheared portion of tissue.

Furthermore, in accordance with some embodiments of the present invention, the biopsy collection chamber may include a sieve for capturing pieces of tissue from the sheared portion.

Furthermore, in accordance with some embodiments of the present invention, the surgical tool may include a vacuum pump configured to suck the portion into the first lumen at the distal end prior to shearing the portion with the surgical blade.

Furthermore, in accordance with some embodiments of the present invention, the surgical tool may include a vacuum pump configured to suck the sheared portion through the first lumen into a biopsy collection chamber.

Furthermore, in accordance with some embodiments of the present invention, the surgical tool may include an infusion tube in the body of the surgical tool coupled to the second lumen at the proximal end of the cannula assembly through the one or more outer hub holes.

Furthermore, in accordance with some embodiments of the present invention, the surgical tool may include an irrigation fluid inlet formed in the body of the surgical tool and coupled to the infusion tube.

Furthermore, in accordance with some embodiments of the present invention, the flexible sheath may include outlet holes into the second lumen near the distal end of the cannula assembly such that irrigation fluid introduced through the irrigation fluid inlet in the body of the surgical tool may pass through the outlet holes at the distal end to irrigate the target surgical site.

Furthermore, in accordance with some embodiments of the present invention, the surgical tool may include a button that may be pushed by a user to toggle between cutting, aspiration, or infusion functions at the target surgical site.

There is further provided, in accordance with some embodiments of the present invention, a method for shearing tissue at a target surgical site. The method may include navigating a distal end of a cannula assembly of a surgical tool to a target surgical site, where the surgical tool may include the cannula assembly, a surgical blade, a connector hub, and an axial ball joint. The cannula assembly with the distal end and a proximal end, including an elongated tube within a flexible sheath along a longitudinal axis passing axially through a first lumen of the elongated tube, wherein a second lumen is formed between the sheath and the elongated tube along the longitudinal axis. The surgical blade may be coupled to the elongated tube at the distal end. The connector hub attached to a body of the surgical tool may include a central inner hub hole and one or more outer hub holes coupled to the cannula assembly at the proximal end. The elongated tube may be placed within the central inner hub hole in the connector hub. The one or more outer hub holes in the connector hub are coupled to the second lumen. The axial ball joint in the body of the surgical tool, may be coupled to the elongated tube at the proximal end of the cannula assembly, that when rotated, causes the surgical blade at the distal end to rotate about the longitudinal axis. The method may include shearing a portion of tissue at the target surgical site by rotating the axial ball joint.

Furthermore, in accordance with some embodiments of the present invention, shearing the portion of the tissue may include excising eye tissue from a trabecular network of an eye.

Furthermore, in accordance with some embodiments of the present invention, the method may include obtaining a biopsy sample by applying a vacuum to the first lumen, so as to suck the sheared portion trough the first lumen into a biopsy collection chamber.

Furthermore, in accordance with some embodiments of the present invention, the method may include irrigating the target surgical site with irrigation fluid passing through outlet holes in the flexible sheath from the second lumen near the distal end of the cannula assembly.

Furthermore, in accordance with some embodiments of the present invention, the method may include sucking the portion of eye tissue at the target surgical site into the first lumen at the distal end prior to shearing the portion with the surgical blade.

Furthermore, in accordance with some embodiments of the present invention, the method may include, within a predefined time interval after sucking the tissue portion into the first lumen at the distal end, shearing the tissue portion with the surgical blade at the target surgical site and irrigating the target surgical site with irrigation fluid.

BRIEF DESCRIPTION OF THE DRAWINGS

In order for the present invention, to be better understood and for its practical applications to be appreciated, the following Figures are provided and referenced hereafter. It should be noted that the Figures are given as examples only and in no way limit the scope of the invention. Like components are denoted by like reference numerals.

FIG. 8A schematically illustrates a side view of a third embodiment of a surgical tool, in accordance with some embodiments of the present invention;

FIG. 8B schematically illustrates a perspective view of a third embodiment of a surgical tool, in accordance with some embodiments of the present invention;

DETAILED DESCRIPTION OF THE INVENTION

Figure 1:
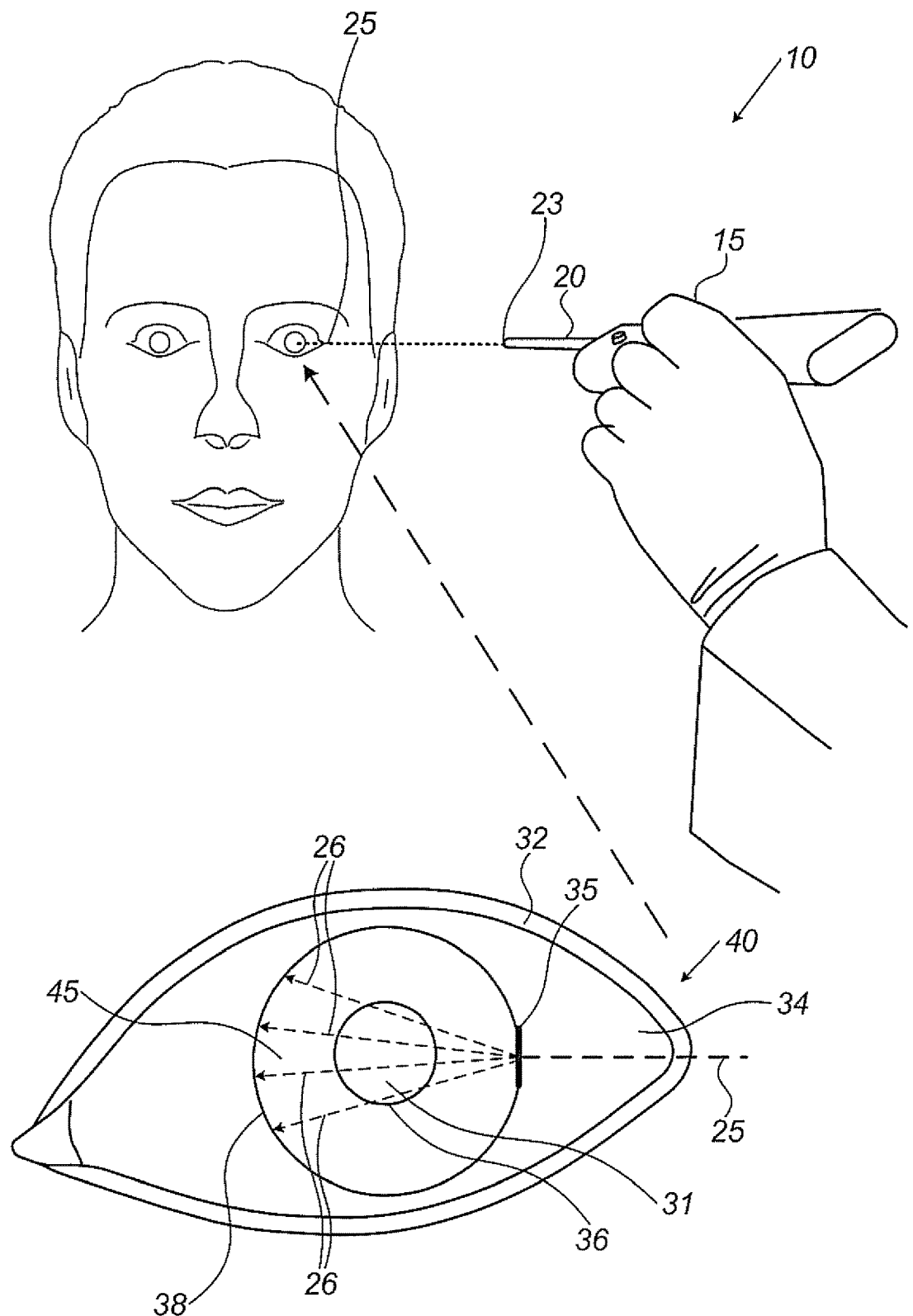
FIG. 1 schematically illustrates a hand of a doctor holding a surgical instrument performing a Minimally Invasive Trabeculotomy (MINT) on an eye, in accordance with some embodiments of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The tennis "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, use of the conjunction "or" as used herein is to be understood as inclusive (any or all of the stated options).

Embodiments of the present invention herein describe a surgical tool for shearing tissue at a target surgical site. The surgical tool may include a cannula assembly with a distal end and a proximal end, a cannula opening into a lumen of the cannula assembly at the distal end, a cutting device coupled at the distal end and within the cannula opening; and an axial ball joint in the surgical tool, coupled to the proximal end of the cannula assembly, that when rotated, causes die cutting device at the distal end to rotate about a longitudinal axis passing axially through the lumen of the cannula assembly, so as to shear a portion of tissue at a target surgical site.

In some embodiments of the present invention, the sheared tissue portion may be used as a biopsy sample for pathology analyses. The surgical tool may be used to separate layers of tissue at any location in a body of a subject. The surgical tool, for example, may be used to remove a top layer of tissue and leave bottom layers of tissue intact at a target surgical site. In addition to using the surgical tool for eye surgeries and eye biopsy sample acquisition as shown hereinbelow, it may also be used, for example, in vacuum assisted biopsies, cancer biopsies, or dermatological biopsies.

Embodiments of the present invention hereinbelow further describe a minimally invasive surgical instrument, which may be inserted through a small corneal incision to ablate a portion of the trabecular meshwork of the eye, thereby allowing for aqueous drainage in the treatment of glaucoma. Tissue removal may be achieved by mechanical means or other tissue destruction techniques.

The surgical instrument may also include an aspiration system. The aspiration system may be configured to remove ablated tissue, gas and bubble formation, and all intraocular debris generated. Trabecular meshwork tissue removed may be collected in a biopsy chamber for further analysis.

The surgical instrument may also be coupled to an infusion system to maintain and deepen the anterior chamber, so that easy access of the angle of the eye is obtained to the trabecular meshwork and Schlemm's canal. Infusion also allows fluid to flow out to the collector channels while the surgery is being performed, thus keeping the surgical site blood free and allowing the surgeon a clear view.

This surgical instrument provides a simple surgical solution for glaucoma treatment. It creates fenestrations of the Schlemm's canal like ELT, but with a much simpler and cheaper instrument. In some embodiments, the surgical instrument may combine the ease of use of mechanical devices such as the istent inject (Glaukos corporation) and the Hydrus stent (Ivantis), but does not leave any device in place which can potentially become blocked by iris or cause damage to the cornea. Other Microinvasive Glaucoma Surgery (MIGS) treatments, which bypass the TM and leave no device behind such as a Kahook Dual Blade (KDB), for example, are difficult to use. This may cause significant damage to the SC and may be more likely to cause damage to the neighboring tissue (e.g., iridodialysis and Descemet's membrane detachment) than a targeted and precise surgical trephining procedure. The Ab interno canalplasty procedure (ABiC) requires more expensive and sophisticated equipment and is technically more difficult to perform, however, it does retain the advantage that it may potentially be the only MIGS procedure that does expand the collector channels as well.

In summary, as a composite procedure that offers some of the advantages of the ELT procedure such as precise TM targeting and proven long term IOP control with cost savings and ease of use of the mechanical TM MIGS, this composite procedure offers some promise as a unique procedure, which is unhindered by prior art. This also strikes a balance between the more surgically destructive angle procedures like Gonioscopically assisted transluminal trabeculotomy (GATT) and KDB as well as the precise, but more unpredictable and expensive devices such as istent inject. Furthermore, if lower IOPs are to be achieved, one cannot implant more istent injects as these would be more expensive, but Minimally Invasive Trabeculotomy (MINT) as a repeatable procedure may deliver more trephines of the TM without additional cost. Thus, an optimum circumference of TM that may be targeted, or an optimum number of holes may be made. If an istent is inserted incorrectly, then it is nonfunctioning and that opportunity is lost. However, if a trephine is incorrectly sited, another is simply made in the right place thereby making the learning curve less steep.

The surgical instrument described herein based on clinical indications as described above may treat all forms of primary open angle glaucoma. In a similar manner to other MIGS, it may be suitable for treating the opened-up angle or the accessible part of the TM in angle closure glaucoma, but more likely to be successful as there is no bulky device left in situ to become blocked by iris or potentially cause chronic inflammation and its sequelae.

There are a variety of TM MIGS procedures on the market. With regard to the amount to TM excised or treated. MINT delivers more than istent inject and equivalent to the KDB, but not as much as the Gonioscopically assisted transluminal trabeculotomy (GATT) or Trab 360 procedure, which targets 360 degrees of the TM. With regard to ease of use, MINT is easier to perform than ABiC and Hydrus but may be slightly more difficult than istent inject. With regard to slow visual recovery due to blood in the anterior chamber, this would be less than KDB and GATT, but maybe equivalent to istent inject and Hydrus, in that there are similarly only small holes to let out blood as opposed to removal of large segments of the TM.

The main disadvantages of MINT compared to competing non TM MIGS devices such as Xen 45 (Allergan), Innfocus Microshunt, and CyPass (Alcon), for example, are the ability to lower the IOP to less than episcleral venous pressure, (e.g., 11 mm Hg). However, as a version of TM MIGS, conversely, they do have the advantage that the IOP will not drop below this level, leading to hypotony with sight threatening visual complications either. These unpredictable complications are difficult to avoid and require further surgery to manage. This hypotony cannot happen with TM MIGS.

In the embodiments of the present invention, the surgical instrument device may have the following characteristics, which may be achieved by appropriate device design, so as to reduce adjacent tissue damage, such as:

Ease of insertion: small tip profile of the surgical instrument device to be inserted through a 2.65 mm corneal wound.

Ease of ablation: cannula with a fixed cutting blade or cutting wire within hollow inner chamber, which can be inserted perpendicularly/tangential to the trabecular meshwork of the eye, and rotated along the longitudinal axis to provide a sheering action. Alternatively, a laser beam transmitted through the cannula may be used to ablate the target tissue.

Ease of aspiration: the ability to extract excised trabecular meshwork with minimal tissue manipulation or damage to surrounding tissue.

Minimal damage: The cannula tip outer wall profile may be curved inwards to prevent damage to surrounding trabecular meshwork even when the cannula tip is abraded across tissue surface.

The surgical instrument device for handheld ambidextrous one-handed use may have a form factor of a pistol, or a pen grip.

The surgical instrument device may be battery operated and fully portable.

The surgical instrument device may include a biopsy chamber for excised trabecular meshwork biopsy collection.

The surgical instrument device may include an optional infusion port which may be coupled to an infusion system to maintain and deepen the anterior chamber, and to irrigate the surgical site to keep the area blood free.

The surgical instrument device may include a cannula assembly, which may be a disposable, medically approved material for transient surgical use in the eye with a cutting blade or a cutting wire radially extended within cannula tip and flushed lip against the cannula tip.

The cannula may have a "dual hub" mechanism including two luer-lock junctions to form separate and independent chambers when connected to the handheld surgical tool.

The cannula may include a soft inflatable and flexible sheath wrapping along its length so as to provide infusion, wherein the irrigation fluid may be channeled out from one or more holes in the sheath near the distal end.

Embodiments of the present invention described herein relates to an ophthalmic surgical instrument and method for the treatment of glaucoma. The glaucoma may be various forms of open angle glaucoma (OAG). The method for the treatment of glaucoma may include the removal of a few small discrete portions of the trabecular meshwork (TM) by mechanical cutting, shearing, cautery, ablation, vaporization or any other suitable tissue destruction technique thus enabling unimpeded channels from the anterior chamber of the eye to the SC. The method also includes aspiration and collection of the excised tissue biopsy.

In some embodiments of the present invention, the surgical instrument may optionally include an apparatus to provide infusion into the anterior or posterior chamber of the eye.

In some embodiments of the present invention, the surgical instrument may include a disposable cannula attached to a handheld, portable surgical device. In other embodiments, the cannula may be disposable. The disposable cannula may be made from a disposable medically approved material for transient surgical use in the eye, with a cutting blade, or cutting wire radially extended within cannula tip and flush against with cannula tip. When inserted perpendicularly and tangentially to the trabecular meshwork of the eye and an aspiration may be applied by the handheld device, a portion of trabecular meshwork will be sucked into the cannula. The cannula may then be rotated along its longitudinal axis, so as to provide a shearing action with a clean ablation of trabecular meshwork within the hollow chamber. This shearing action may then be repeated on other points of the TM according to the desired TOP reduction.

The cannula may be accompanied by a tube miming parallel to the channel infusion, which maintains and deepens the anterior chamber, and irrigates the surgical site, so as to keep the area blood free for increased visibility. In another embodiment, a soft inflatable sheath (e.g. silicon) wrapping around the cannula may be used to provide infusion, where the irrigation fluid may be channeled out from holes formed in the sheath near the cannula tip.

In yet another embodiment, the cannula may be a laser probe capable of substantially complete tissue removal by cautery, vaporization, or other tissue destructive techniques. A fiber may be held within the probe, which directs light energy to the distal end of the probe tip, in close proximity of the trabecular meshwork to allow for cautery or vaporization of the tissue. The cannula with infusion capabilities may have a small tip profile for insertion through a 2.65 mm corneal wound.

In some embodiments of the present invention, the surgical instrument may be a battery operated handheld tool, which operates and controls the rotation of the cannula and infusion rate of irrigation fluid. The surgical instrument may include an electrical rotor for manipulating the cannula and enabling shearing of the TM tissue. The surgical instrument may include a collection chamber for the containment of the excised trabecular meshwork.

In some embodiments of the present invention, the surgical instrument may include a pump system to control aspiration or infusion, a battery to allow for portable operation, one of more trigger buttons to toggle the activation of the rotation and infusion, and an irrigation inlet, which may be optionally connected to either a separate infusion system, or embodied within the device. The surgical instrument may have a form factor of a pistol or a pen grip, or any other form factor suitable ambidextrous one-handed use.

In operation, the surgical instrument may provide IOP lowering effects by removing a portion of the trabecular meshwork, allowing free access of aqueous humor from the anterior chamber through to the Schlemm's canal that connects to the episcleral venous system, thereby to general circulatory system of the body. Multiple ablation sites may be performed at different clock hours (e.g., at different angles) radially around the meshwork (e.g., around eye 40) for a larger drainage area so as to ensure exposing one or more of the collector channels.

The method for glaucoma treatment using the surgical tool as described herein is a simple, effective, low cost, minimally invasive, non-implantable glaucoma treatment option.

FIG. 1 schematically illustrates a hand 10 of a doctor holding surgical instrument 15 performing a Minimally Invasive Trabeculotomy (MINT) on an eye 40, in accordance with some embodiments of the present invention. Surgical instrument 15 may also be referred to and used interchangeably herein as a MINT surgical instrument, a surgical tool, or a MINT surgical tool. Surgical instrument 15 may include a cannula assembly 20, typically a disposable attachment, with a distal end 23. Cannula assembly 20 may be configured to be inserted obliquely along an axis 25 into eye 10 via au incision 35 through a cornea 45. Eye 40 as shown at the bottom of FIG. 1 includes an eyelid 32, a sclera 34, a pupil 31, and a corneal limbus 38 (e.g., corneal-scleral junction).

Figure 2:
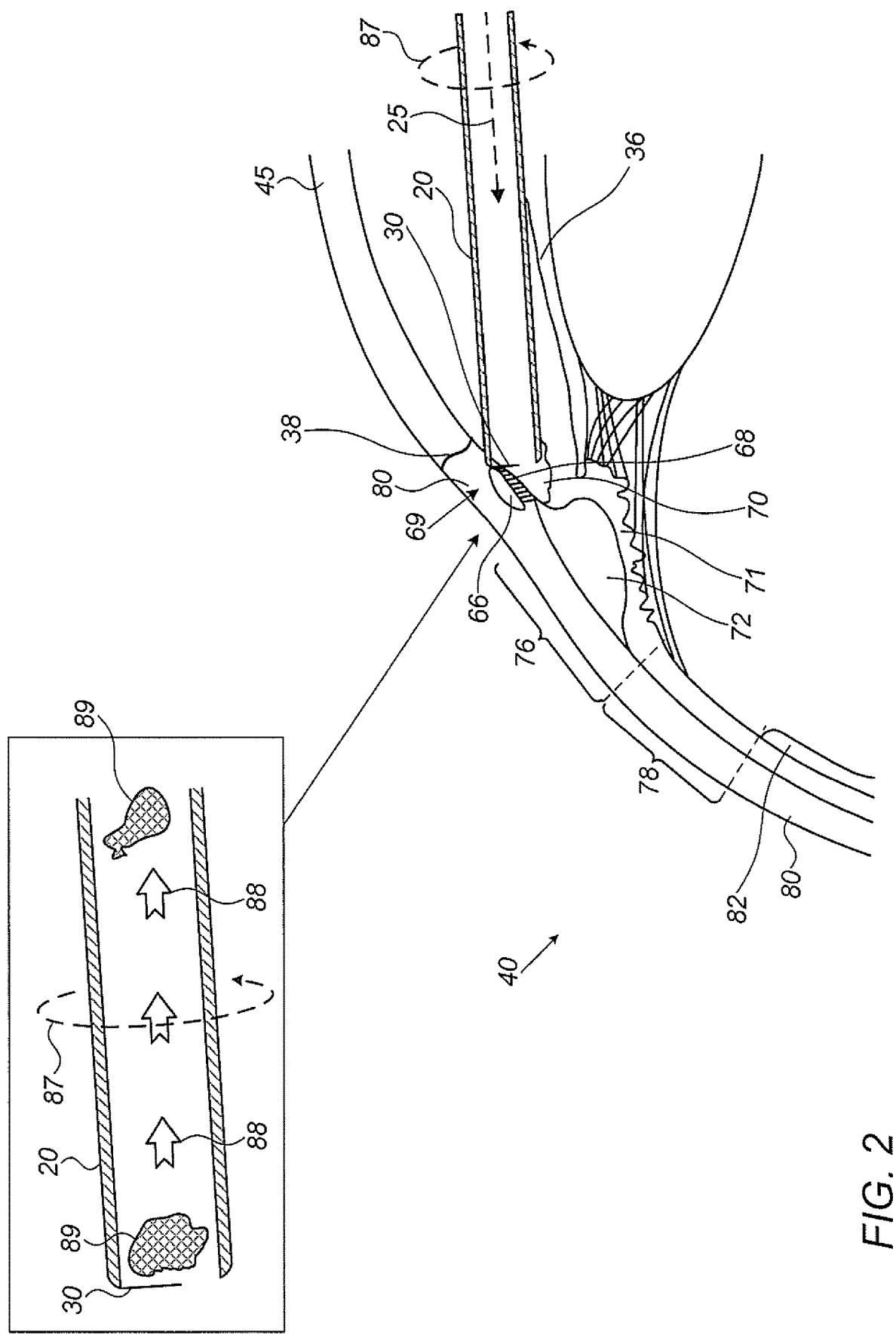
FIG. 2 schematically illustrates an enlarged view of an eye with a distal end of a cannula assembly positioned perpendicularly to a section of a trabecular meshwork, in accordance with sonic embodiments of the present invention.

FIG. 2 schematically illustrates an enlarged view of eye 40 with distal end 23 of cannula assembly 20 positioned perpendicularly to a section of trabecular meshwork 68, in accordance with some embodiments of the present invention. FIG. 2 schematically illustrates anatomical features in eye 40. These anatomical features may include cornea 45 Schlemm's canal 66, trabecular meshwork 68, an iridocorneal at 70, a ciliary epithelium 71, a ciliary muscle 72, corneal limbus 38, iris 36, a pars plicata 76, a pars plana 78, a sclera 80, and a retina 82.

In some embodiments of the present invention, cannula assembly 20 may be inserted through corneal wound incision 35, typically with a length of 2.65 mm, for example along axis 25. Corneal wound incision 35 may be made at any suitable place on cornea 45, typically near corneal limbus 38. Distal end 23 may be placed perpendicularly and tangentially to trabecular meshwork 68 of eye 40 (e.g., the target surgical site as shown by an arrow 69 in FIG. 2) at different points along trabecular meshwork 68 as shown by arrows 26 in FIG. 1. Arrows 26 may represent different trajectories of axis 25 through corneal wound incision 35 as the doctor navigates distal tip 23 of surgical tool 15 within the anterior chamber. Distal end 23 may include a blade 30 of any suitable configuration. When the cannula assembly 20 may be rotated, typically by 360 degrees along longitudinal axis 25 as shown in by an arrow 87, a portion 89 of tissue of trabecular meshwork 68 may be excised. Portion 89 of eye tissue may be used as a biopsy tissue sample for examination to determine if glaucomatous or any other pathologic tissue may be present, for example.

In some embodiments of the present invention, surgical instrument 15 may be used to ablate portion 89 of trabecular meshwork 68 of eye 40, so as to increase aqueous humor drainage and reduce IOP in the treatment of glaucoma.

In some embodiments of the present invention, surgical instrument 15 may include an aspiration system, such as a vacuum pump, for example, for aspirating excised biopsy tissue sample 89 along axis 25 by creating a vacuum 88 as shown by arrows. The aspiration system may be designed to remove ablated tissue, gas and bubble formation, as well as all other intraocular debris created during the surgical procedure. In other embodiments, the use of surgical instrument 15 is not limited to biopsies of the eyes glaucoma eye diseases, but may be used to collect biopsy samples for any other type of eye diseases (e.g., to excise any type of eye tissue).

Additionally, the aspiration system may be used in assisting the acquisition of biopsy tissue 89 from the trabecular meshwork. For example, vacuum 88 may suck the tissue into cannula assembly 20 where blade 30 may be rotated 360 degrees to twist and/or shear off the tissue sample where vacuum 88 may suck biopsy sample 89 into a collection chamber. In some embodiments, surgical instrument 15 may include a collection chamber for collecting aspirated biopsy tissue sample 89.

In some embodiments of the present invention, surgical tool 130 may be coupled to an infusion system to inject irrigation fluid into eye 40, so as to maintain and deepen the anterior chamber of eye 40 during the procedure. The deepen anterior chamber of eye 40 enables the ophthalmologic surgeon to insert distal end 23 into eye 40 along axis 25 with easy access to trabecular meshwork 68 and Schlemm's canal 66. The irrigation fluid may be channeled out from distal end 23 of cannula assembly 20 while the surgery may be performed thus keeping the surgical site blood-free and may allow the surgeon to have a clear view of the surgical site. Stated differently, the irrigation fluid may be used to prevent the eye from collapsing during the medical procedure due to a loss of fluid, such as aqueous humor, for example.

In some embodiments, the irrigation fluid, or infusion fluid may include a balanced salt solution (BSS) for infusion. In other embodiments, the irrigation fluid may include medication that may be introduced into the eye during the medical procedure.

In some embodiments of the present invention, a time delay (e.g., a predefined time interval) between applying a vacuum to the tissue at the target surgical site and initiating rotation of the blade and infusion for washing the blood from the target surgical site may be used. A time delay in the range 0-1 seconds may ensure that enough negative pressure accumulates on the tissue at the target surgical site for sucking the tissue into distal end 23 before shearing the tissue with the cutting blade.

Figure 3A:
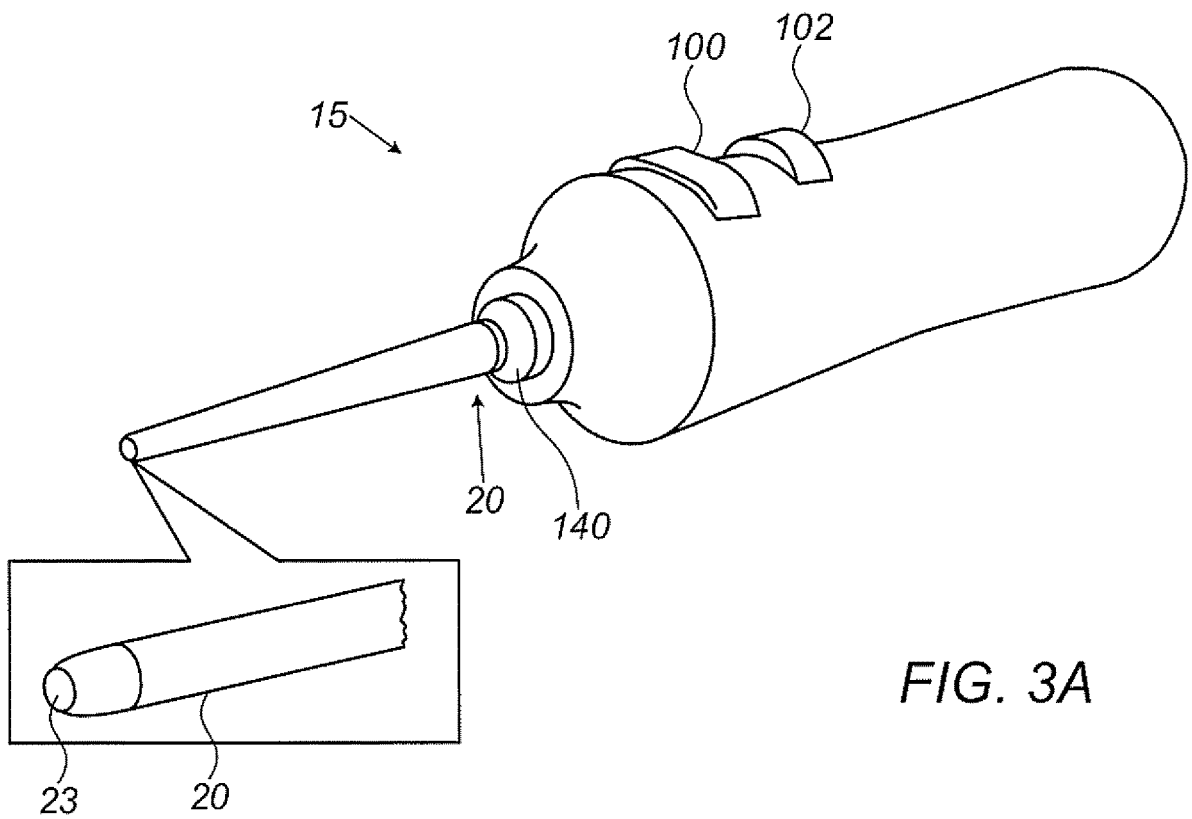
FIG. 3A schematically illustrates a first embodiment of surgical tool with a pen grip form factor, in accordance with some embodiments of the present invention.

FIG. 3A schematically illustrates a first embodiment of surgical tool 15 with a pen grip form factor, in accordance with some embodiments of the present invention. The pen grip form factor may permit ambidextrous one-handed use. Surgical tool 15 with the pen grip form factor may include cannula assembly 20 that rotates about a cannula hub 140, which is connected to the hand held portion of the surgical tool. In some embodiments, buttons 100 and 102 of surgical tool 15 may be assigned to activate a rotation/aspiration function and an infusion function.

In other embodiments, surgical tool 15 may have one or two buttons. In embodiments where one button is used, the one button may be toggled by the doctor between rotation, aspiration and/or infusion functions, for example. In some embodiments, the one button may not be present on the body of surgical tool 15, but may be>implemented as a foot pedal, or an activation pedal, that may be coupled to surgical tool 15 to be used by a user (e.g., a doctor) so as to toggle between the rotation (e.g., cutting), aspiration and/or infusion functions of surgical tool 15.

For example, after a surgeon creates a 1.8-2.7 mm incision on the cornea with a scalpel, the surgeon may insert distal end 23 of surgical tool 15 and navigate distal end 23 to the target surgical site (e.g., the trabecular mesh) and then operate the device by pushing the one button to toggle between the rotation (e.g., cutting), aspiration and/or infusion functions at the target surgical site.

Figure 3B:
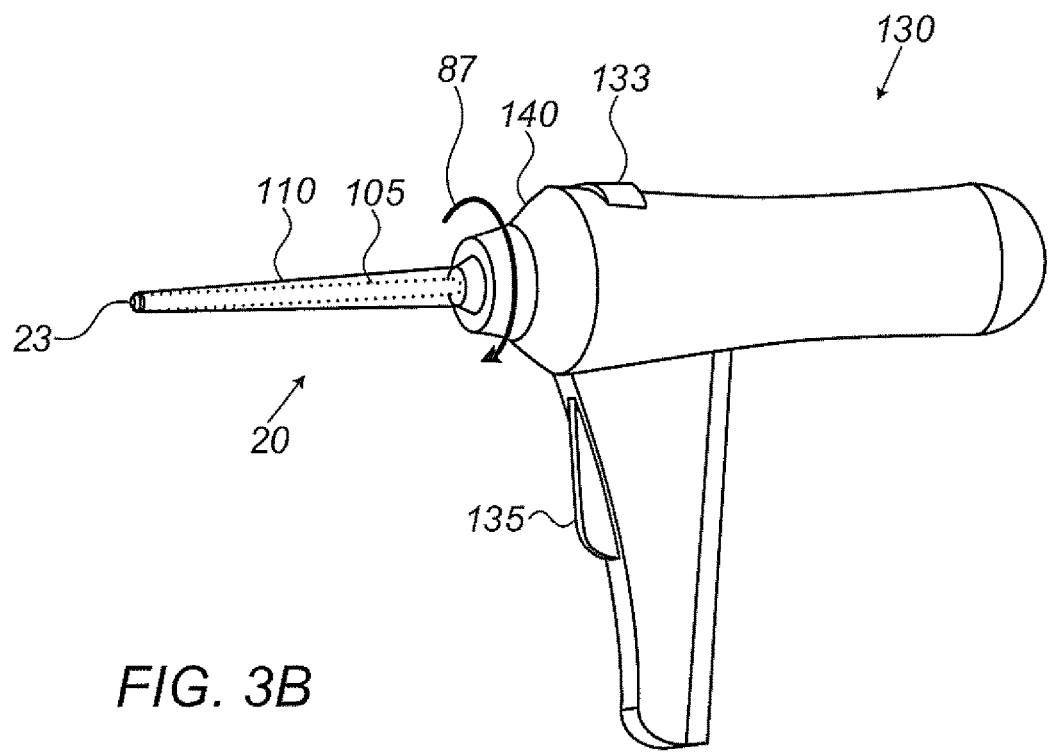
FIG. 3B schematically illustrates a second embodiment of surgical tool with a pistol form factor, in accordance with some embodiments of the present invention.

FIG. 3B schematically illustrates a second embodiment of surgical tool 130 with a pistol form factor, in accordance with some embodiments of the present invention. In some embodiments, surgical tool 130 may include cannula hub 140, cannula assembly 20 with distal end 23, and a trigger 135. Cannula assembly 20 may include an inflatable sheath 110 and a cannula 105 with blade 30 at distal end 23. Cannula 105 may be connected to cannula hub 140 at a proximal end. Buttons 133 and 135 of surgical tool 130 may be assigned, for example, to activate a rotation/aspiration function and/or an infusion function.

Figure 4A:
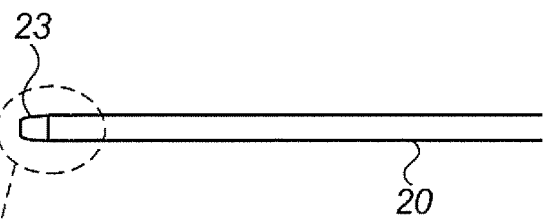
FIG. 4A schematically illustrates a cannula assembly, in accordance with some embodiments of the present invention.

FIG. 4A schematically illustrates cannula assembly 20, in accordance with some embodiments of the present invention. A typical length of biopsy cannula assembly 20 is 20-25 mm.

Figure 4B:
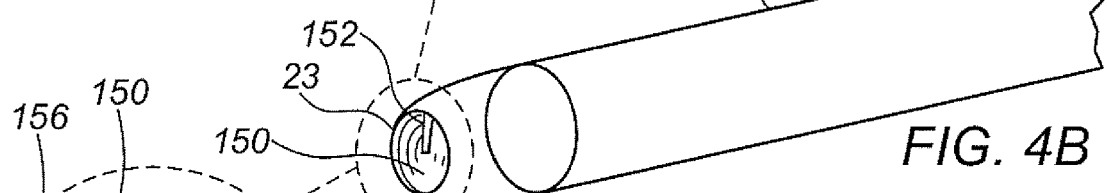
FIG. 4B schematically illustrates a cannula assembly with a cutting blade, in accordance with sonic embodiments of the present invention.

FIG. 4B schematically illustrates cannula assembly 20 with a cutting blade 152, in accordance with some embodiments of the present invention. This blade trephine embodiment may include blade 152 with an opening 150 with cross-sectional diameter typically 0.5 mm or larger.

Figure 4D:
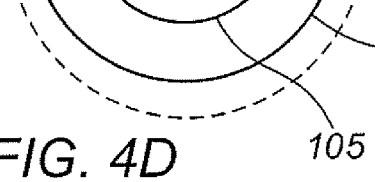
FIG. 4D schematically illustrates a cross-sectional view of a distal end of cannula assembly with a blade, in accordance with some embodiments of the present invention.
Figure 4C:
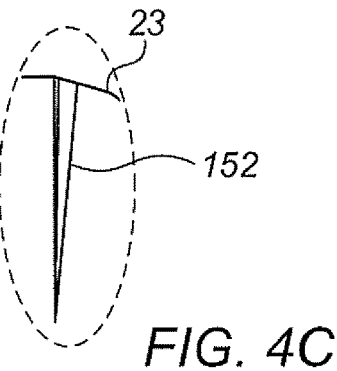
FIG. 4C schematically illustrates au enlarged view of blade, in accordance with some embodiments of the present invention.

FIG. 4C schematically illustrates an enlarged view of blade 152, in accordance with some embodiments of the present invention. An opening 150 into the lumen of cannula 105 behind blade 152.

FIG. 4D schematically illustrates a cross-sectional view of distal end 23 of cannula assembly 20 with blade 152, in accordance with some embodiments of the present invention. Opening 150 may have a typical diameter of 0.5 mm or larger (e.g., diameter of cannula 105). The distance from the cannula wall to the outer edge of cannula assembly 20 may typically be 0.15 mm as shown by arrow 156. The width of blade 152 at marker 154 as shown in FIG. 4D may typically be 0.22 mm. Blade 152 may extend radially mid-way within cannula tip (e.g., distal end 23) and may be flush with or positioned close to cannula opening 150. The cutting edge of the blade is parallel to cannula opening 150.

In some embodiments of the present invention, the cannula tip curved profile may be curved inward at distal end 23 to prevent damage to the surrounding trabecular meshwork outside of the surgical site even when cannula distal end 23 may be abraded across the tissue surface at the surgical site during the operation. Blade 152 may be fixed to the inner wall of cannula assembly 20, such that any tissue within the opening 150 will be twisted and/or sheared off when the cannula assembly 20 is rotated 360 degrees.

Figure 4E:
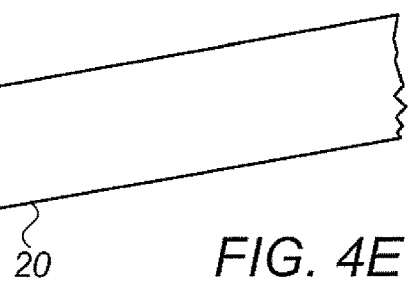
FIG. 4E schematically illustrates a cannula assembly with a cutting wire, in accordance with some embodiments of the present invention.

FIG. 4E schematically illustrates cannula assembly 20 with a cutting wire 160, in accordance with some embodiments of the present invention. This embodiment illustrates an alternate wire trephine design where blade 30 may include cutting wire 160.

Figure 4F:
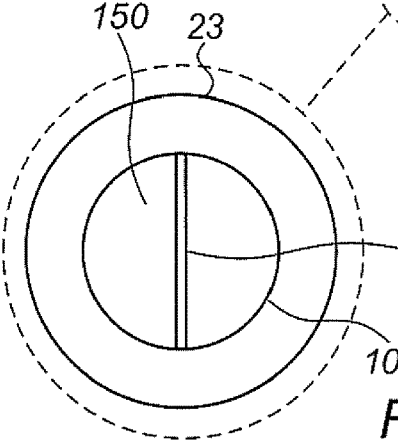
FIG. 4F schematically illustrates a cross-sectional view of a distal end of a cannula assembly with a cutting wire, in accordance with some embodiments of the present invention.

FIG. 4F schematically illustrates a cross-sectional view of distal end 23 of cannula assembly 20 with cutting wire 160, in accordance with some embodiments of the present invention. Cutting wire 160 may fully extend radially across the inner diameter of cannula opening 150 to provide shearing of the trabecular meshwork when rotated. As in the blade trephine embodiment, the cannula tip outer wall profile may be curved inward to prevent damage to the surrounding trabecular meshwork outside of the surgical site even when cannula distal end 23 may be abraded across the tissue surface at the surgical site. The width of cutting wire 160 may be typically 0.5 mm or larger.

Figure 5A:
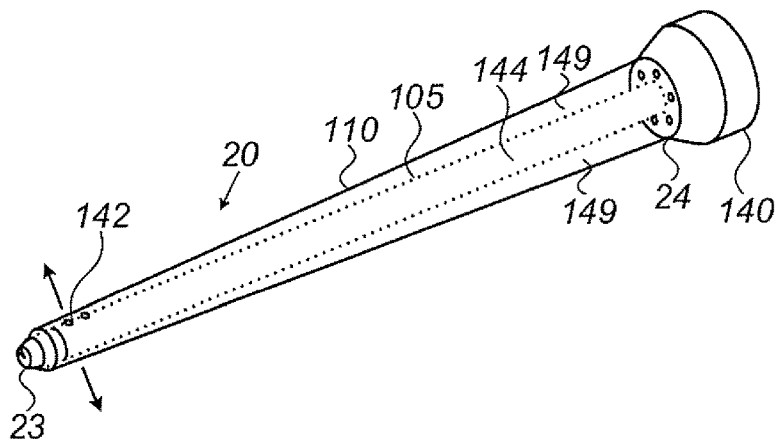
FIG. 5A schematically illustrates a cannula assembly with an inflatable sheath attached to a cannula hub, in accordance with some embodiments of the present invention.

FIG. 5A schematically illustrates cannula assembly 20 with inflatable sheath 110 attached to cannula hub 140, in accordance with some embodiments of the present invention. Cannula 105 may include a first lumen 144. A second lumen 149 is formed between sheath 110 and cannula 105 (e.g., an elongated tube 105).

Figure 5B:
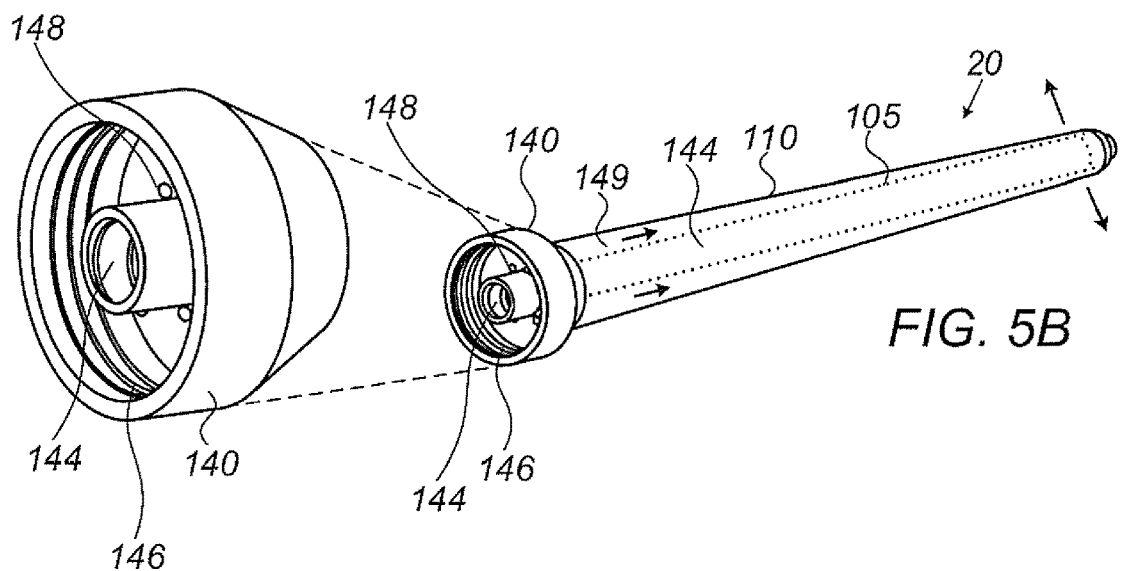
FIG. 5B schematically illustrates a right perspective view of a cannula assembly attached to a cannula hub, in accordance with some embodiments of the present invention.

FIG. 5B schematically illustrates a right perspective view of cannula assembly 20 attached to cannula hub 140, in accordance with some embodiments of the present invention.

Figure 5C:
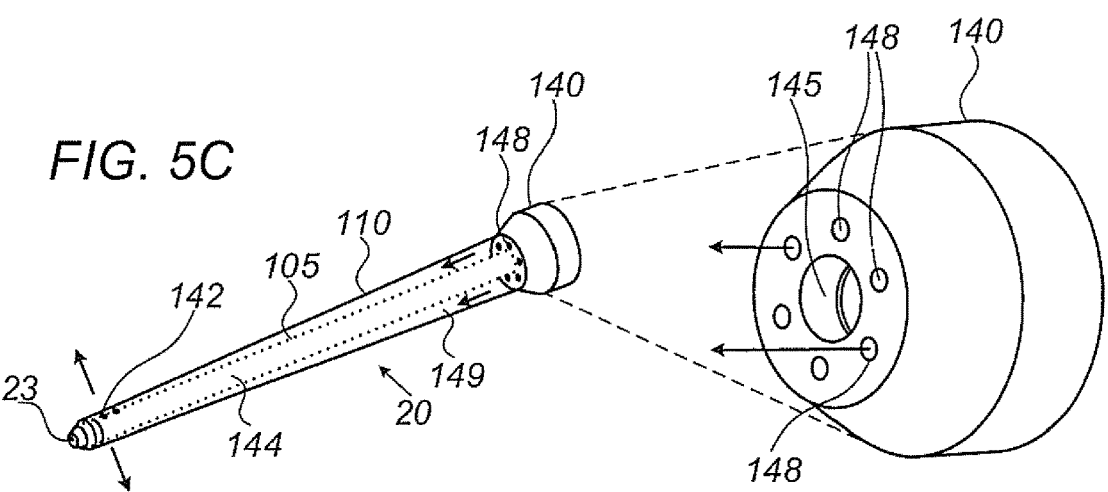
FIG. 5C schematically illustrates a left perspective view of a cannula assembly attached to a cannula hub, in accordance with some embodiments of the present invention.

FIG. 5C schematically illustrates a left perspective view of cannula assembly 20 attached to cannula hub 140, in accordance with some embodiments of the present invention.

In some embodiments of the present invention, cannula assembly 20 may include cannula 105 attached to cannula hub 140. In other embodiments, cannula assembly 20 may include a soft inflatable sheath wrapping to (e.g., sheath 110) to provide infusion where the irrigation fluid may be channeled out from one of more outlet holes 142 near distal end 23.

In some embodiments of the present invention, the soil inflatable sheath wrapping may be in a form of a tube running parallel (e.g., sheath 110) to cannula 105 to channel the infusion liquid into the chamber of eye 40. The direction of the infusion liquid flow in sheath 110 and out of outlet holes 142 (e.g., via second lumen 149) may be seen in both FIGS. 5B and 5C by the arrows. Cannula hub 140 may be attachable to the surgical tool 15 and one or more holes 148 in cannula hub 140 may allow the irrigation fluid to flow into sheath 110 of cannula assembly 20 via holes 148.

Similarly, sheared tissue sample 89 from trabecular meshwork 68 may be aspirated through first lumen 144 of cannula 105 from distal end 23. Sheared tissue sample 89 may be transported by vacuum 88 through first lumen 144 to a proximal end 24 of cannula 105 where first lumen 144 is coupled to a central hole 145 in cannula hub 140 in a manner permitting rotation 87 of cannula 105. Threading 146 in cannula hub 140 may be used to join and fix to cannula hub 140 to a locking interface on surgical tool 15. Sheared tissue sample 89 may be transported into a biopsy collection chamber in surgical tool 15.

In the embodiments shown in FIGS. 5A-5C, cannula hub 140 may include two luer-lock junctions to form separate and isolated chambers when connected to surgical handheld device 15. The two isolated chambers (e.g., first lumen 144 and second lumen 149) allow the independent flow of irrigation fluid within the outer hub via the one or more holes 148 out to sheath 110, and aspiration through cannula first lumen 144.

Figure 6:
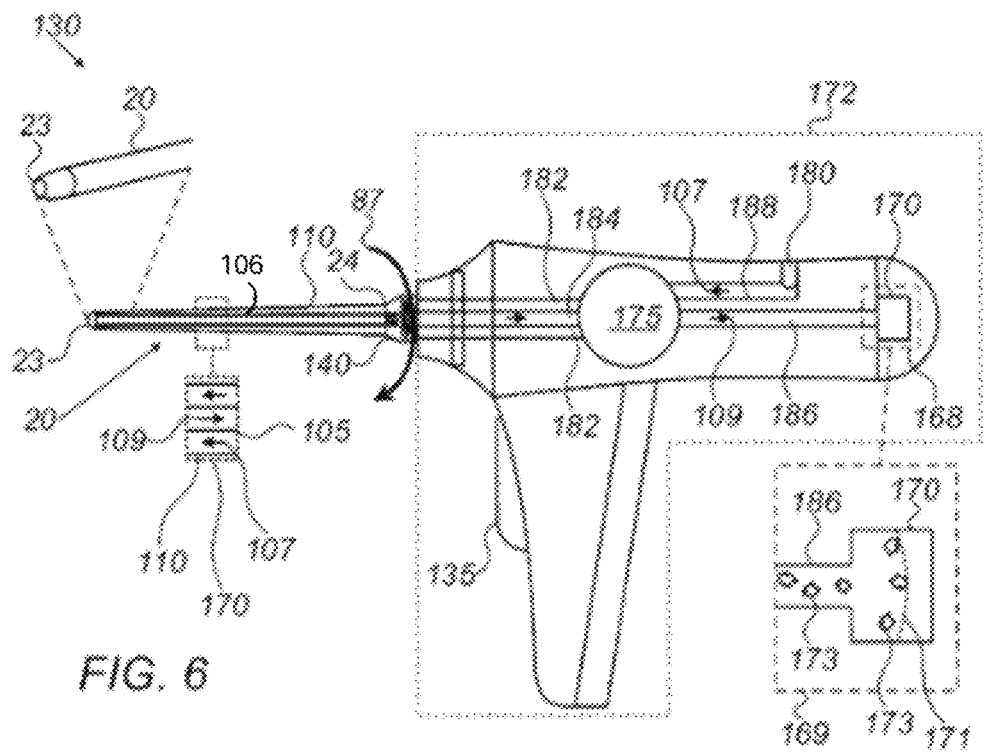
FIG. 6 schematically illustrates a cross-sectional side view of a surgical tool with a pistol form factor, in accordance with some embodiments of the present invention.

FIG. 6 schematically illustrates a cross-sectional side view of surgical tool 130 with a pistol form factor, in accordance with some embodiments of the present invention. Surgical tool 130 may include cannula assembly 20 with distal end 23 and proximal end 24 connected to cannula hub 140. Cannula hub 140 may be attached to a body 172 of surgical tool 130. The elements of body 172 ate shown inside the box defined with a dotted line as shown in FIG. 6. Body 172 may include trigger 135, an axial ball joint 175 for 360-degree rotation of cannula 105, a biopsy collection chamber 170, and an irrigation fluid inlet 180 for introducing irrigation fluid for balanced salt solution (BSS) drip infusion, for example. In body 172, irrigation fluid may flow from inlet 180 into an infusion tube 188 coupled to axial ball joint 175.

In some embodiments, as shown in an inset 169, biopsy collection chamber 170 may include a sieve 171 for capturing pieces 173 of tissue from the sheared portion 89 that may break into pieces 173 while traveling from distal end 23 and before reaching biopsy collection chamber 170. Sieve 171 may be of any suitable size and/or shape for improving flow rate. Sieve 171 may have a hemispherical shape as shown in FIG. 6. Sieve 171 may be flat, conical (e.g., triangular), or dome shaped. Sieve 171 may be a membrane with partial coverage within biopsy collection chamber 170. It may be placed at the entrance to biopsy collection chamber 170 or may be positioned anywhere within biopsy collection chamber 170. Sieve 171 may include holes as shown as the gaps in the dotted line representing sieve 171. The holes in sieve 171 may be circular or square shaped, each hole ranging in size from 20 µm to 1 mm.

In some embodiments of the present invention, axial ball joint 175 (or any suitable similar mechanism) may be used to rotate 87 the cannula 105 while pumping irrigation fluid into sheath 110, while channeling ablated tissue sample 89 into biopsy collection chamber 170 via tubes 184 and 186 in body 172. Tube 184 may be coupled to first lumen 144. Axial ball joint 175 pumps the irrigation fluid into a tube 182 (e.g., a continuation of infusion tube 188) coupled to cannula hub 140 and into the proximal end of sheath 110 via holes 148. The irrigation fluid may be pumped from proximal end 24 to distal end 23 of cannula assembly 20 in sheath 110, so as to exit from the one of more outlet holes 142 near distal end 23 into the surgical site.

Insert 106 in FIG. 6 illustrates a cross-section of cannula assembly 20 with arrows 107 showing the direction the irrigation fluid in sheath 110, and an arrow 109 showing the direction of aspiration (e.g., vacuum 88) in cannula 105 (e.g., in fast lumen 144).

Figure 7A:
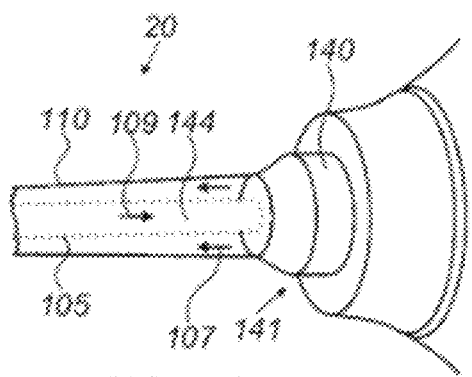
FIG. 7A schematically illustrates a locking interface, in accordance with some embodiments of the present invention.

FIG. 7A schematically illustrates a locking interface 141, in accordance with some embodiments of the present invention.

Figure 7B:
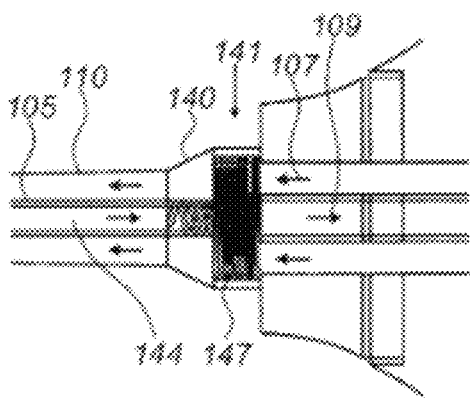
FIG. 7B schematically illustrates a cross-sectional view of a locking interface, in accordance with some embodiments of the present invention.

FIG. 7B schematically illustrates a cross-sectional view of locking interface 141, in accordance with some embodiments of the present invention.

Handheld surgical tool 130 and 15 may include locking interface 141 for attaching or screwing cannula hub 140 of cam la assembly 20 (e.g., threading 146) onto a male type connector (or any suitable mating connector) on body 172 with threading 147 so as to attach and hold the disposable cannula assembly to the body of the MINT surgical instrument. The dual hub design shown in FIGS. 7A and 7B of the disposable cannula (e.g., cannula 105) allows the independent and separate flow 107 of irrigation fluid (e.g., infusion) within second lumen 149 in outer sheath 110 and aspiration flow 109 in first lumen 144 of cannula 105.

In some embodiments of the present invention, surgical tool 130 may include an electrical motor to rotate the cannula and enable shearing of the biopsy tissue at the surgical site.

In some embodiments of the present invention, surgical tool 130 may include a pump system to form vacuum 88 in first lumen 144, so as to suck biopsy tissue sample 89 into biopsy collection chamber 170 for collecting the trabecular meshwork biopsy sample.

In some embodiments of the present invention, irrigation inlet 180 may be connected to a separate infusion system, or may be included in surgical tool 130 itself.

In some embodiments of the present invention, trigger 135 may be used to toggle the activation of the cannula rotation and infusion of irrigation fluid to the surgical site.

In some embodiments of the present invention, trigger 135 may be used to activate the rotation of cannula 105 and the suction of biopsy sample 89 into biopsy collection chamber 170.

In some embodiments of the present invention, a liquid-air membrane or valve may be used to separate biopsy collection chamber 170 and a vacuum system.

In some embodiments of the t invention, surgical tool 130 may include a battery for portable operation.

In some embodiments of the present invention, trigger 135 may be positioned at the front of body 172 of surgical tool 130 for finger operation as shown in FIG. 6. In other embodiments, trigger 135 may be positioned at the back of body 172 of surgical tool 130 for thumb operation.

In some embodiments of the present invention, a peristaltic pump may be located in body 172 between inlet 180 and biopsy collection chamber 170 so as to eliminate the need for a liquid-air membrane or valve mechanism.

In some embodiments of the present invention, surgical tool 130 may include one or more finger grips when surgical tool 130 may be operated as a syringe.

In some embodiments of the present invention, surgical tool 130 may have infusion provided by a tithe running parallel to cannula 105.

FIG. 8A schematically illustrates a side view of a third embodiment of a surgical tool 200, in accordance with some embodiments of the present invention.

FIG. 8B schematically illustrates a perspective view of a third embodiment of surgical tool 200, in accordance with some embodiments of the present invention.

Surgical tool 200 may include a cannula assembly 210 with an outer tube 214 as shown in an inset 212, a stepper motor 216, a back cup adapter 218, an end cup fixation screw 220, an air/vacuum tube swivel connector 222, a deep groove flanged ball bearing 224 for supporting tube 210 while rotating, a front bearing adapter 226, a second deep groove flanged ball bearing 228, a front connecting tube 230, a body 232 (e.g., surgical tool outer shell), an end cup 234, an electric power line 236, and a vacuum line 240.

In various embodiments, cannula assembly 210 may be formed from a surgical steel 23G tube with welded on cutting features. Outer tube 214 may be formed from a surgical steel 19G tube. Stepper motor 216 may include a 20 mm hollow shaft stepper motor. Back cup adapter 218 may include a nylon friction coupling device—clamps, cutter tube, motor and swivel connector. End cup fixation screw 220 may include an M3 screw. Air/vacuum tube swivel connector 222 may be a 6 mm Air/vacuum tube swivel connector. Front bearing adapter 226 may be formed from a precision milled stainless hollowed shaft. Front connecting tube 230 may include a nylon friction coupling device clamps, cutter tube, motor and swivel connector. Electric power line 236 may include a JST2.0 PH 6 pins to 4 pins type electrical line. Vacuum line 240 may include a 6×4 mm air/vacuum line.

Figure 9A:
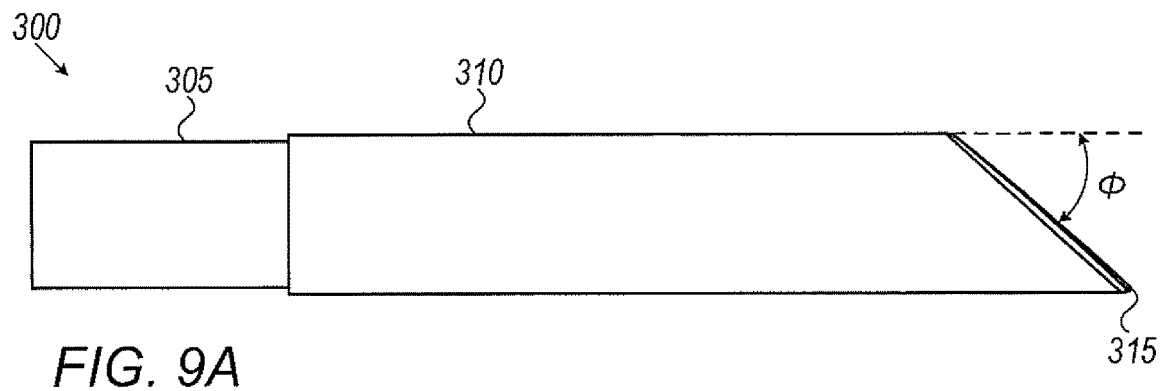
FIG. 9A schematically illustrates a side view of a second embodiment of a cannula assembly, in accordance with some embodiments of the present invention.

FIG. 9A schematically illustrates a side view of a second embodiment of a cannula assembly 305, in accordance with some embodiments of the present invention.

Figure 9B:
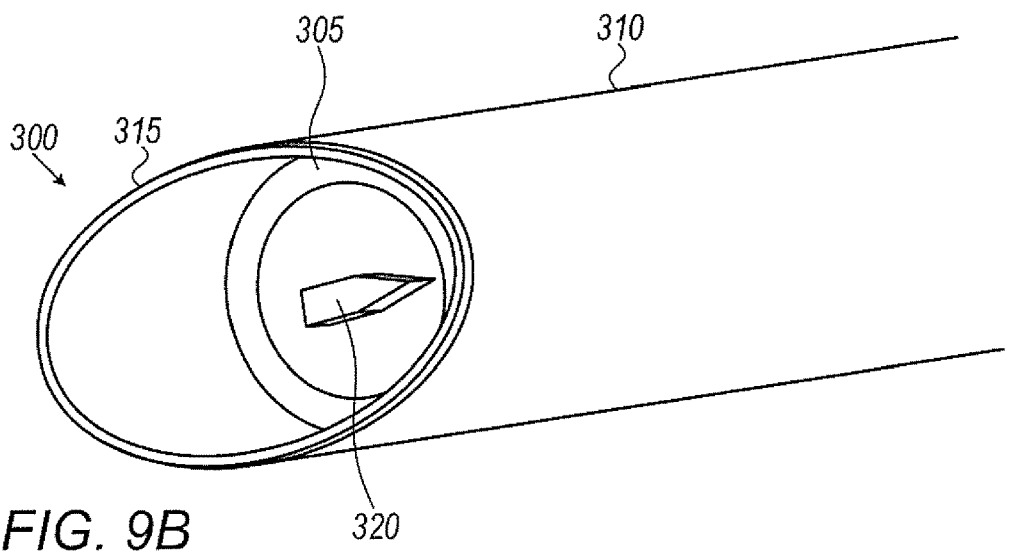
FIG. 9B schematically illustrates a perspective view of a second embodiment of a cannula assembly, in accordance with some embodiments of the present invention.

FIG. 9B schematically illustrates a perspective view of a second embodiment of cannula assembly 305, in accordance with some embodiments of the present invention.

Figure 9C:
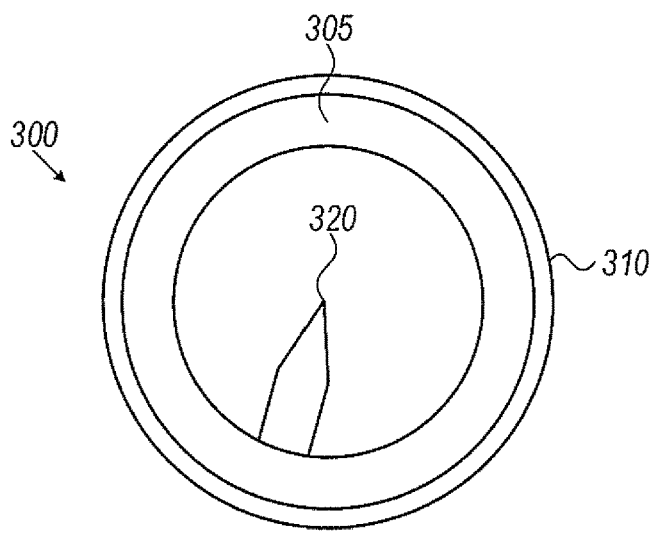
FIG. 9C schematically illustrates a cross-sectional view of a second embodiment of a cannula assembly, in accordance with some embodiments of the present invention.

FIG. 9C schematically illustrates a cross-sectional view of a second embodiment of cannula assembly 305, in accordance with some embodiments of the present invention.

In some embodiments of the present invention, a distal end 300 of cannula assembly 305 (e.g., inner tube 305) may be placed within an outer tube 310 passing axially along a longitudinal axis through the cannula opening. A cutting blade 320 may be placed flush or near the cannula opening (e.g., at a slight distance 0-10 mm away from the cannula opening) as shown in FIG. 9C. Cannula assembly 305 may be rotatable within outer tube 310. In some embodiments, outer tube 310 may not be rotatable or fixed in place so as to avoid inducing disturbances in the surrounding tissue near the target surgical site and to merely provide better suction at a distal tip 315 contacting the tissue at the target surgical site.

In some embodiments of the present invention, distal end 300 of cannula assembly 305 may have a distal tip 315 that is beveled where an angle y shown in FIG. 9A may be in the range of 0-90 degrees. The beveled tip may provide a more uniform suction when distal tip 315 when contacting eye tissue at typical angles in the peripheral anterior chamber of the eye.

Figure 10:
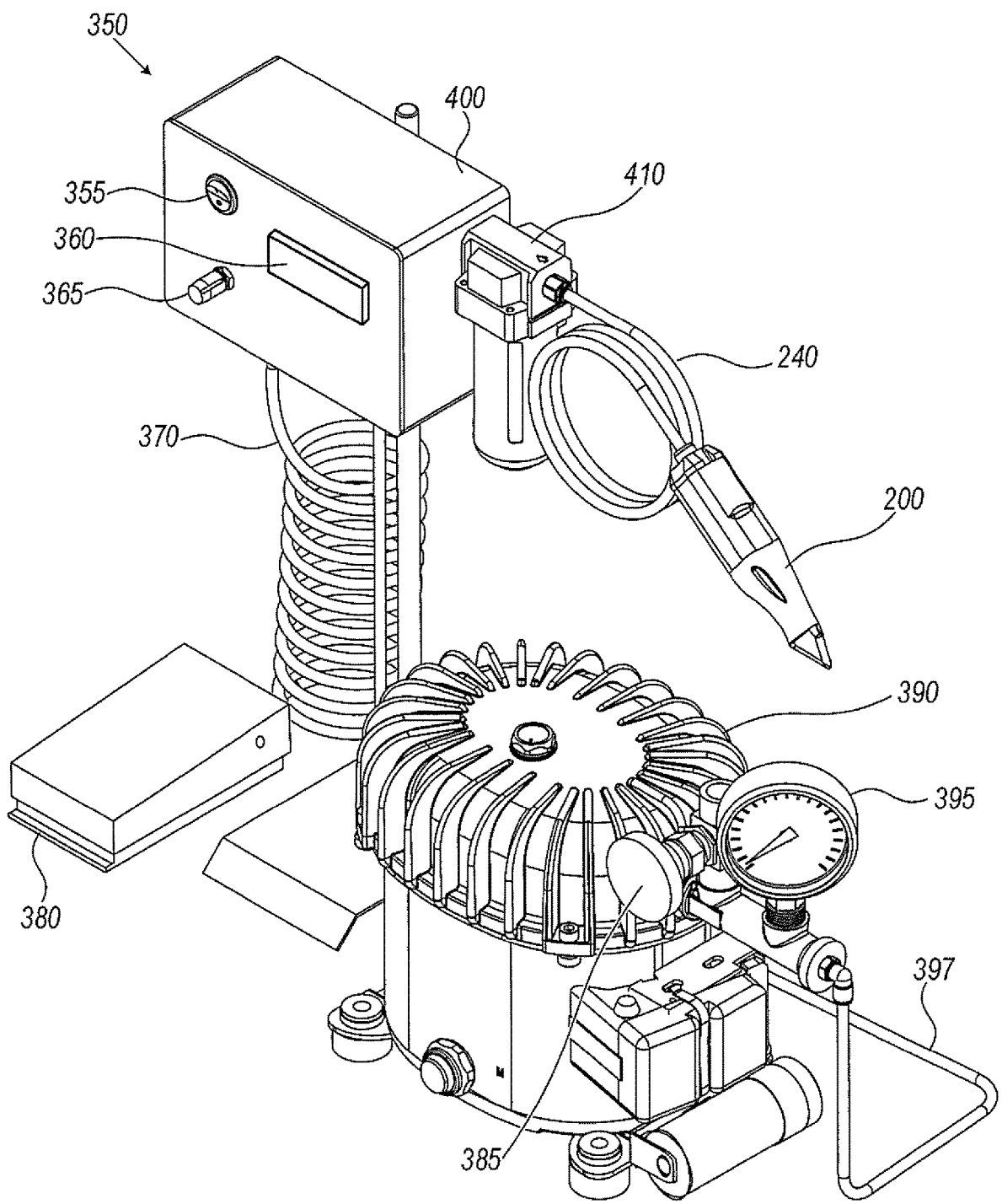
FIG. 10 schematically illustrates a system for controlling a surgical tool for shearing tissue at a target surgical site, in accordance with some embodiments of the present invention.

FIG. 10 schematically illustrates a system 350 for controlling surgical tool 200 for shearing tissue at a target surgical site, in accordance with some embodiments of the present invention. System 350 may be used, for example, to performing a Minimally Invasive Trabeculotomy (MINT) on an eye of a patient. System 350 may include a control box 400 coupled to vacuum line 240 of surgical tool 200 (e.g., as shown in FIGS. 8A and 8B) via a fluid separator 410. Control box 400 may include an ON/OFF switch 355, an LCD display 360, and a control knob 365 for controlling the rotation speed of blade 30 cannula assembly 210). A vacuum pump 390 may be coupled to control box 400, where vacuum pump 390 may include a vacuum regulating valve 385, a vacuum gauge 395 and a vacuum inlet 397. An activation (foot) pedal 380 may be coupled to control box 400 via a pedal control line 370. Activation pedal 380 may be used by a user (e.g., a doctor) for controlling surgical tool 200. Activation pedal 380 may be used to toggle between the rotation (e.g., cutting), aspiration and/or infusion functions of surgical tool 200.

In some embodiments of the present invention, surgical tool 15 may include a laser generator and a cannula. The cannula may be a laser probe capable for the substantially complete tissue removal by ablation, vaporization or cautery. The laser probe may include a fiber to direct light energy to the distal end of the probe tip and into the surgical site (e.g., in close proximity to the trabecular meshwork to allow for cautery or vaporization of the tissue.) Surgical tool 15 may include an infusion/aspiration inlet, which may be optionally connected to a separate infusion system.

In some embodiments of the present invention, surgical tool 15 may include a laser generator and a cannula. The cannula may be a laser probe capable for the substantially complete tissue removal by ablation, vaporization or cautery. However, one or more optical fibers for conducting the laser beam may be arranged for example, in a bundle. The bundle may be held together with cladding may be used to direct light energy to the distal end of the probe tip and into the surgical site (e.g., in close proximity to the trabecular meshwork to allow for cautery or vaporization of the tissue.)

In some embodiments of the present invention, a surgical tool for shearing tissue at a target surgical site may include a cannula assembly with a distal end and a proximal end, a cannula opening into a lumen of the cannula assembly at the distal end a cutting device coupled at the distal end and within the cannula opening, and an axial ball joint in the surgical tool, coupled to the proximal end of the cannula assembly, that when rotated, causes the cutting device at the distal end to rotate about a longitudinal axis passing axially through the lumen of the cannula assembly, so as to shear a portion of tissue at a target surgical site.

In some embodiments of the present invention, the target surgical site may be a trabecular meshwork of an eye of a subject.

In some embodiments of the present invention, the distal end of the cannula assembly may have a curved inward tip profile.

In some embodiments of the present invention, the distal end of the cannula assembly may have a beveled tip.

In some embodiments of the present invention, the surgical tool may include an outer tube, where the cannula assembly may be placed within the outer tube passing axially along the longitudinal axis and the cannula assembly is rotatable within the outer tube.

In some embodiments of the present invention, the outer tube may not be rotatable.

In some embodiments of the present invention, the cutting device may extend radially mid-way within the cannula or may be flush with the cannula opening.

In some embodiments of the present invention, the cutting device may be a surgical cutting blade.

In some embodiments of the present invention, a surgical tool for shearing tissue at a target surgical site may include cannula assembly 20. Cannula assembly 20 with distal end 23 and proximal end 24, may include an elongated tube (e.g., cannula 105) within flexible sheath 110 along longitudinal axis 25 passing axially through first lumen 144 of elongated tube 105, wherein second lumen 149 is formed between sheath 110 and elongated tube 105 along longitudinal axis 25. Surgical blade 30 may be coupled to elongated tube 105 at distal end 23. Connector hub 140 may be attached to body 172 of the surgical tool may comprise central inner hub hole 145 and one or more outer hub holes 148 coupled to cannula assembly 20 at proximal end 24. Elongated tube 105 may be placed within central inner hub hole 145 in connector hub 140. One or more outer hub holes 148 in connector hub 140 may be coupled to second lumen 149. Axial ball joint 175 in body 172 of the surgical tool, may be coupled to elongated tub 105 at proximal end 24 of cannula assembly 20, that when rotated 87, causes surgical blade 30 at distal end 23 to rotate 87 about longitudinal axis 25, so as to shear portion 89 of tissue at a target surgical site.

In some embodiments of the present invention, the sheared portion may include eye tissue excised from a trabecular meshwork of eye 40.

In some embodiments of the present invention, the surgical tool may include a biopsy collection chamber in the body for collecting the sheared portion of tissue.

In some embodiments of the present invention, the biopsy collection chamber may include a sieve for capturing pieces of the tissue from the sheared portion.

In some embodiments of the present invention, the surgical tool may include a vacuum pump configured to suck the portion into the first lumen at the distal end prior to shearing the portion with the surgical blade.

In some embodiments of the present invention, the surgical tool may include a vacuum pump configured to suck the sheared portion through the first lumen into the biopsy collection chamber.

In some embodiments of the present invention, the surgical tool may have a pistol form factor.

In some embodiments of the present invention, the surgical tool may have pen grip form factor.

In some embodiments of the present invention, the surgical blade may extend radially mid-way at an opening into the first lumen at the distal end.

In some embodiments of the present invention, the surgical blade may include a cutting wire.

In some embodiments of the present invention, the surgical tool may include an infusion tube in the body of the surgical tool coupled to the second lumen at the proximal end of the cantina assembly through the one or more outer hub holes.

In some embodiments of the present invention, the surgical tool may include an irrigation fluid inlet formed in the body of the surgical tool and coupled to the infusion tube.

In some embodiments of the present invention, the flexible sheath may include outlet holes into the second lumen near the distal end of the cannula assembly, wherein irrigation fluid introduced through the irrigation fluid inlet in the body of the surgical tool may pass through the outlet holes at the distal end to irrigate the target surgical site.

In some embodiments of the present invention, the surgical tool may include a motor for rotating the axial ball joint.

In some embodiments of the present invention, the distal end is curved inward.

In some embodiments of the present invention, the surgical tool may include a button that may be pushed by a user to toggle between cutting, aspiration, or infusion functions at the target surgical site.

In some embodiments of the present invention, a method for shearing tissue at a target surgical site may include navigating a distal end of a cannula assembly of a surgical tool to a target surgical site, wherein the surgical tool may include:

the cannula assembly with the distal end and a proximal end, may include an elongated tube within a flexible sheath along a longitudinal axis passing axially through a first lumen of the elongated tube, wherein a second lumen is fanned between the sheath and the elongated tube along the longitudinal axis;

a surgical blade coupled to the elongated tube at the distal end;

a connector hub attached to a body of the surgical tool may include a central inner hub hole and one or more outer hub holes coupled to the cannula assembly at the proximal end;

wherein the elongated tube is placed within the central inner hub hole in the connector hub, and wherein the one or more outer hub holes in the connector hub are coupled to the second lumen; and an axial ball joint in the body of the surgical tool, coupled to the elongated tube at the proximal end of the cannula assembly, that when rotated, causes the surgical blade at the distal end to rotate about the longitudinal axis; and shearing a portion of tissue at the target surgical site by rotating the axial ball joint.

In some embodiments of the present invention, shearing the portion of tissue may include excising eye tissue from a trabecular network of an eye.

In some embodiments of the present invention, the method may include obtaining a biopsy sample by applying a vacuum to the first lumen, so as to suck the sheared portion through the first lumen into a biopsy collection chamber.

In some embodiments of the present invention, the method may include irrigating the target surgical site with irrigation fluid passing through outlet holes in the flexible sheath from the second lumen near the distal end of the cannula assembly.

In some embodiments of the present invention, the method may include sucking the portion of eye tissue at the target surgical site into the first lumen at the distal end prior to shearing the portion with the surgical blade.

In some embodiments of the present invention, the method may include, within a predefined time interval after sucking the tissue portion into the first lumen at the distal end, shearing the tissue portion with the surgical blade at the target surgical site and irrigating the target surgical site with irrigation fluid.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A surgical tool for shearing tissue at a target surgical site, the surgical tool comprising:
   a cannula assembly with a distal end and a proximal end, comprising an elongated tube within a flexible sheath along a longitudinal axis passing axially through a first lumen of the elongated tube;
   wherein the distal end of the cannula assembly having a surgical blade and wherein the distal end of the cannula assembly further having an inwardly curved tip; and
   an axial ball joint in a body of the surgical tool, coupled to the elongated tube at the proximal end of the cannula assembly, that when rotated, causes the surgical blade to rotate about the longitudinal axis, so as to shear a portion of tissue at a target surgical site.

2. The surgical tool according to claim 1, wherein the sheared portion comprises eye tissue excised from a trabecular meshwork of an eye.

3. The surgical tool according to claim 1, further comprising a biopsy collection chamber in the body for collecting the sheared portion of tissue.

4. The surgical tool according to claim 3, wherein the biopsy collection chamber comprises a sieve for capturing pieces of tissue from the sheared portion.

5. The surgical tool according to claim 4, wherein the sieve is of hemispherical shape, flat shaped, conical shaped or dome shaped.

6. The surgical tool according to claim 4, wherein the sieve is a membrane with partial coverage within the biopsy collection chamber.

7. The surgical tool according to claim 4, wherein the sieve comprises a plurality of holes.

8. The surgical tool according to claim 1, further comprising a vacuum pump configured to suck the portion into the first lumen at the distal end prior to shearing the portion with the surgical blade.

9. The surgical tool according to claim 1, further comprising a vacuum pump configured to suck the sheared portion through the first lumen into a biopsy collection chamber.

10. The surgical tool according to claim 9, wherein a predefined time interval is used between applying the vacuum to the tissue at the target surgical site and initiating rotation of the blade and infusion for washing blood from the target surgical site.

11. The surgical tool according to claim 1, further comprising a button that may be pushed by a user to toggle between cutting, aspiration, or infusion functions at the target surgical site.

12. The surgical tool according to claim 1, wherein a second lumen is formed between the flexible sheath and the elongated tube along the longitudinal axis.

13. The surgical tool according to claim 12, further comprising an infusion tube in the body of the surgical tool coupled to the second lumen at the proximal end of the cannula assembly through one or more outer hub holes.

14. The surgical tool according to claim 13, further comprising an irrigation fluid inlet formed in the body of the surgical tool and coupled to the infusion tube.

15. The surgical tool according to claim 14, wherein the flexible sheath comprises outlet holes into the second lumen near the distal end of the cannula assembly such that irrigation fluid introduced through the irrigation fluid inlet in the body of the surgical tool may pass through the outlet holes at the distal end to irrigate the target surgical site.

16. The surgical tool according to claim 12, further comprising a connector hub attached to the body of the surgical tool comprising a central inner hub hole and one or more outer hub holes coupled to the cannula assembly at the proximal end; and wherein the elongated tube is placed within the central inner hub hole in the connector hub, and wherein the one or more outer hub holes in the connector hub are coupled to the second lumen.

17. The surgical tool according to claim 1, wherein the flexible sheath is an inflatable sheath.

* * * * *